US006764471B2

(12) United States Patent
Lee (10) Patent No.: US 6,764,471 B2
(45) Date of Patent: Jul. 20, 2004

(54) DENTAL SYRINGE

(76) Inventor: Alexander E. Lee, 10 Giletta Ct., Closter, NJ (US) 07624

( * ) Notice: Subject to any disclaimer, the term of this patent is extended or adjusted under 35 U.S.C. 154(b) by 58 days.

(21) Appl. No.: 10/008,373

(22) Filed: Nov. 13, 2001

(65) Prior Publication Data

US 2003/0069544 A1 Apr. 10, 2003

Related U.S. Application Data

(60) Provisional application No. 60/247,854, filed on Nov. 13, 2000.

(51) Int. Cl.[7] .................................................. A61M 9/00
(52) U.S. Cl. ....................... 604/240; 604/232; 604/413; 604/201; 604/198
(58) Field of Search ................................ 604/187, 413, 604/192, 198, 201, 227, 232, 240

(56) References Cited

U.S. PATENT DOCUMENTS 1,012,700 A * 12/1911 Payne ......................... 604/232
1,532,744 A * 4/1925 Hein .......................... 604/232
3,848,593 A   11/1974 Baldwin ............... 128/218 DA
4,931,040 A * 6/1990 Haber et al. ................ 604/110
5,069,225 A * 12/1991 Okamura ..................... 600/578

* cited by examiner

Primary Examiner—Brian L. Casler
Assistant Examiner—Jeremy Thissell
(74) Attorney, Agent, or Firm—Nolte, Nolte & Hunter (57) ABSTRACT

A syringe, for injecting anesthetic contained in a medicine vial. The syringe includes a housing having a needle end and a plunger end, connected by a body; to which housing is attached a plunger assembly having a plunger at the plunger end. There is a vial slot in the housing, cooperatively sized for receiving a medicine vial. A needle assembly slot is in the body, at the needle end, for receiving a needle assembly from a side of the body. A seat at the needle end of the housing receives and locates a corresponding seat portion of the needle assembly within the housing. Depressing the plunger housingward impales the vial onto a penetrator of the needle assembly and seats the assembly firmly.

7 Claims, 10 Drawing Sheets

Prior Art

DENTAL SYRINGE

CROSS REFERENCE TO RELATED APPLICATION

This application converts Provisional Application No. 60/247,854, filed Nov. 13, 2000, to a utility application and claims priority f under 35 USC 119(e) from that Provisional Application.

BACKGROUND OF THE INVENTION

1. Field of the Invention

The present invention relates to a new type of dental syringe.

2. Description of the Related Art

In the dental syringe art, the conventional syringe is adapted to allow the dentist to retract the syringe plunger after the initial stick, in order to ascertain that he has not hit a blood vessel, by using his thumb in the thumb ring of the syringe, pulling back on the plunger and observing the anesthetic vial to determine if blood has been pulled into the syringe. If it has, this indicates that he must find a new spot for the injection point in order to avoid injecting anesthetic into the bloodstream via a blood vessel. There are two reasons for this:

One is that the anesthetic usually contains epinephrine, which can affect heart rate adversely.

Two, is that if the anesthetic is taken away from the site by the blood vessel, it will fail to anesthetize the site.

Thus, in contrast to the usual medical syringe used by doctors, in which the entire syringe is generally disposable, the dental syringe has a reusable metal framework.

Figure 1:
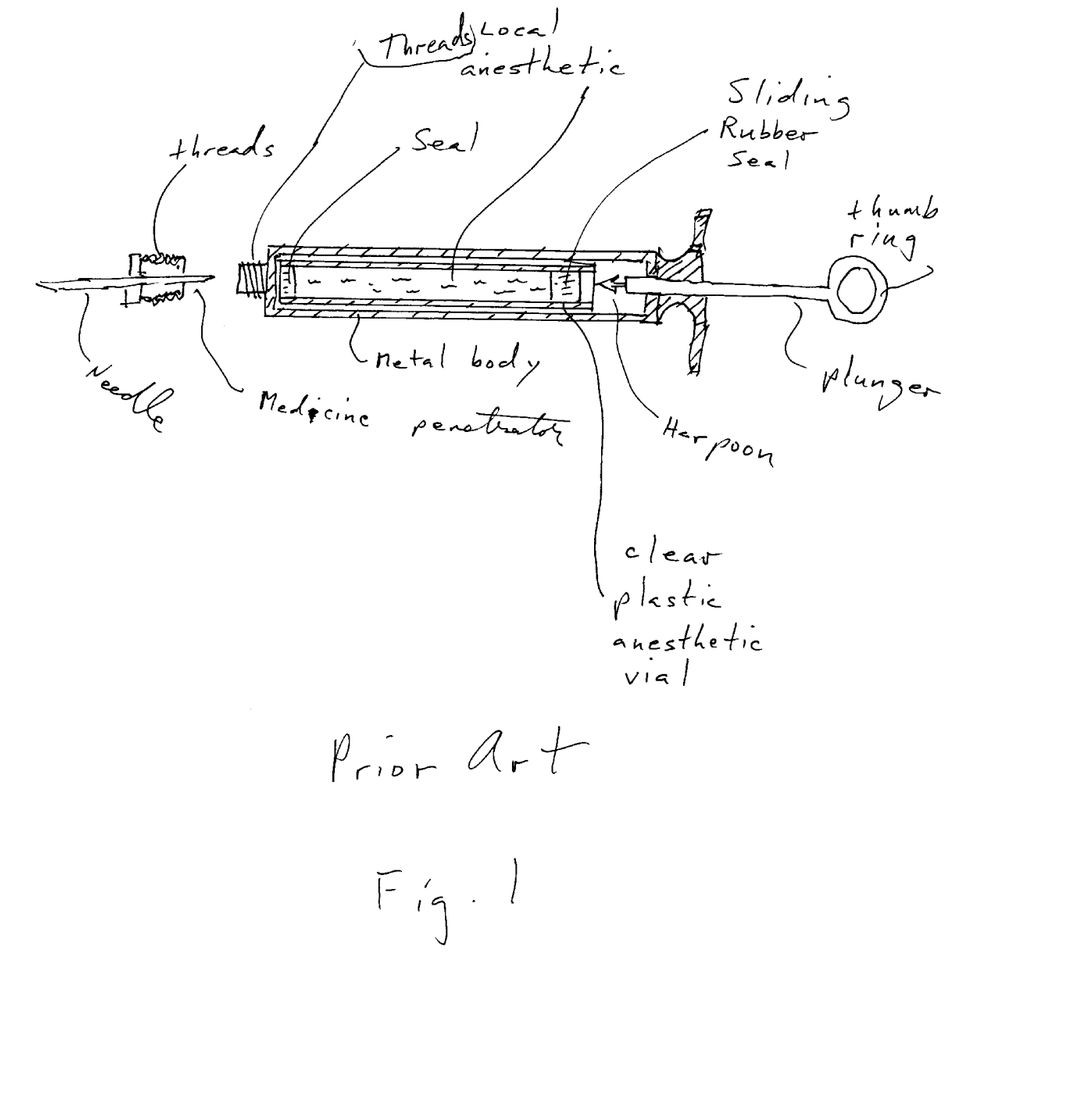
FIG. 1 is an elevation of a syringe in the prior art.

FIG. 1 shows the prior art in which the syringe comprises a metal body which is open on one side to admit a clear plastic anesthetic vial, in the form of a cylinder containing local anesthetic, sealed in by a penetrable seal at the needle end, and by a sliding, flexible seal at the plunger end of the syringe. The plunger comprises a thumb ring, a shaft, and a harpoon at the vial end of the shaft. In operation, the vial is inserted into the metal body. The metal body is placed threaded end down to a surface. An impact is applied to the end of the thumb ring to drive the harpoon into the sliding rubber seal. The needle is then screwed by the screw threads onto this threaded end of the syringe so that the medicine penetrator, which is basically a short needle, penetrates the end seal of the vial. Medicine can now be injected, or the plunger barbs can pull back, to test for the needle point's proximity to a blood vessel, by pulling blood into the medicine vial which will be visible to the dentist.

A problem of the prior art is that the threads of the needle must be a tight fit, which makes the needle quite difficult to remove from the threads of the metal body. This is complicated by the fact that the needle is a sharp object covered with human blood, containing human blood, and presenting a significant biohazard if the operator is stuck by said needle. The operator typically must apply large amounts of force to remove the needle from the metal body, with the operator's hands in close proximity to this hazardous sharp object.

U.S. Pat. No. 3,848,593 to Baldwin refers to an alternative needle securement, but still requires an application of significant rotational torque at the needle.

SUMMARY OF THE INVENTION

The present invention seeks to obviate this problem by having a non-threaded needle mount.

It is an object of the present invention to provide a syringe which obviates the need to apply an unscrewing force in the vicinity of the needle which exceeds the breaking strength of the sharp contaminated needle. The invention provides an easy side loading syringe from which the needle assembly is easily removed.

DETAILED DESCRIPTION OF PREFERRED EMBODIMENTS

Other objects and features of the present invention will become apparent from the following detailed description considered in connection with the accompanying drawings which disclose an embodiment of the present invention. It should be understood, however, that the drawings are designed for the purpose of illustration only and not as a definition of the limits of the invention.

Figure 2:
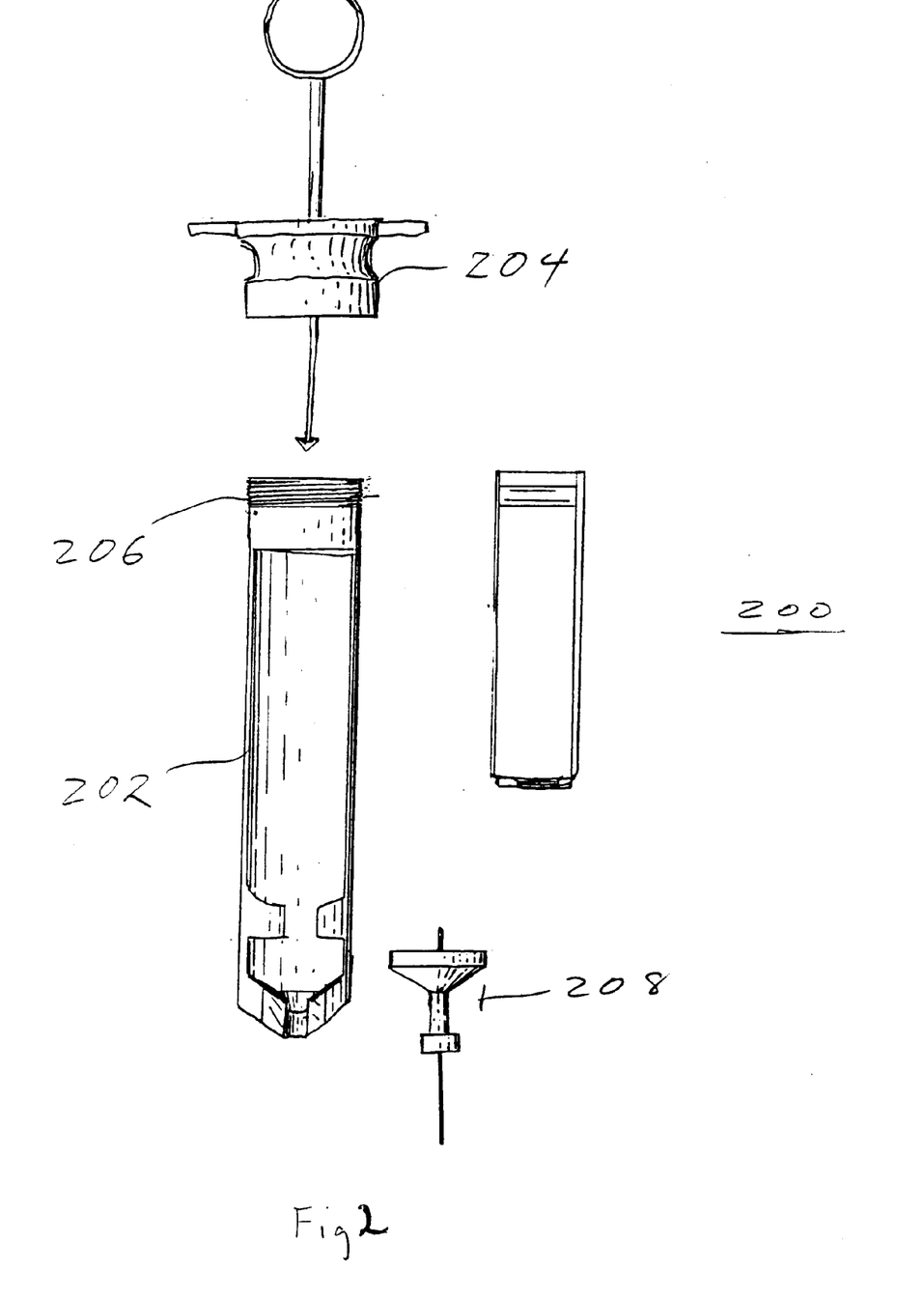
FIG. 2 is an exploded elevation of the separate parts of a syringe of the present invention.
Figure 7:
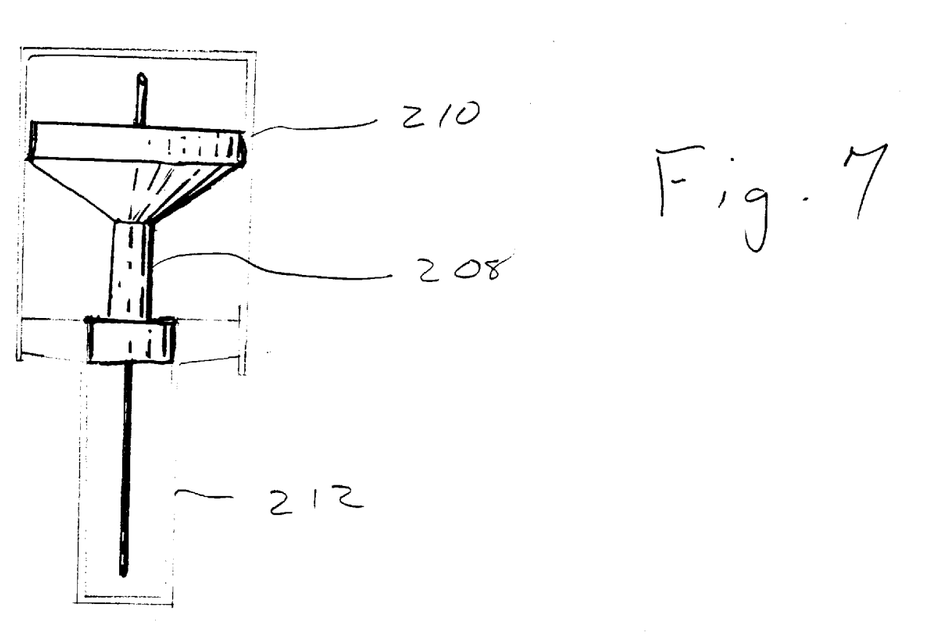
FIG. 7 is a picture of the needle assembly with protective sterile cap.

In the presently preferred embodiment, shown in FIG. 2, the syringe, generally designated 200, comprises a novel housing 202, to which the conventional plunger assembly 204 screws by means of screw threads 206. Needle assembly 208 is shown in its sterile packaging in FIG. 7, comprising a penetrator protector 210 and a needle protector 212.

Figure 3:
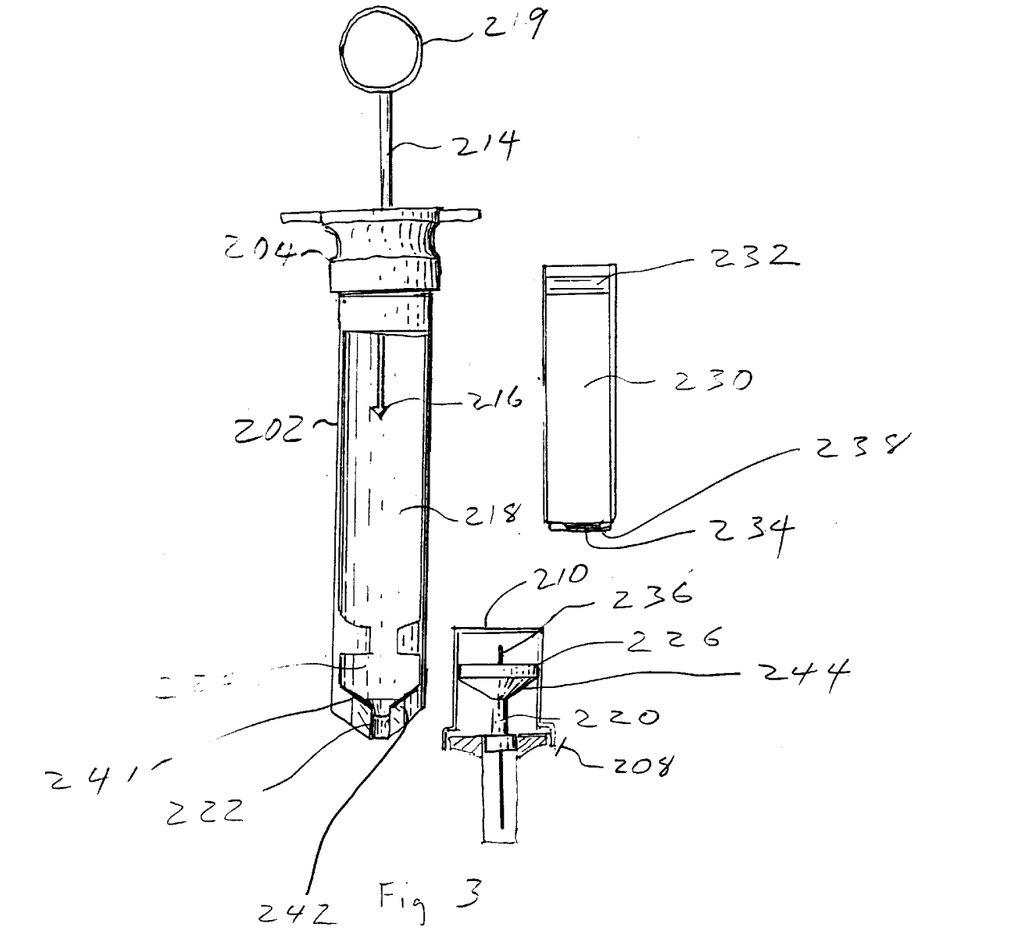
FIG. 3 is a similar elevation of an assembled syringe body.
Figure 4:
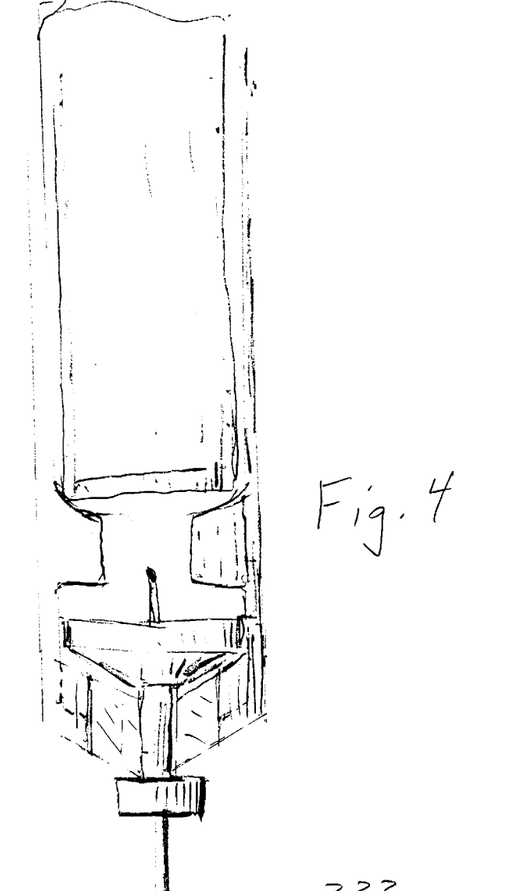
FIG. 4 is an enlarged elevation of the syringe body with the needle assembly being inserted.
Figure 5:
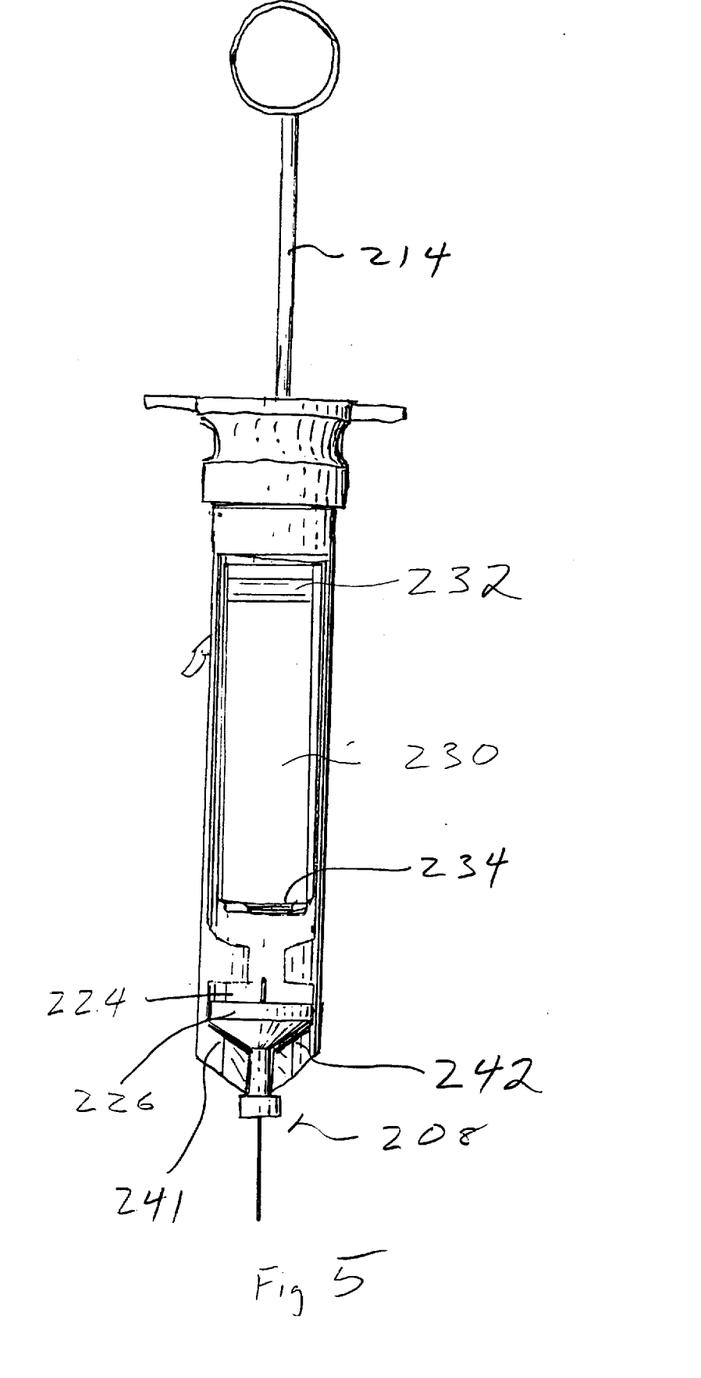
FIG. 5 is an elevation of the syringe with the needle assembly being slid into the syringe.

As shown in FIG. 3, plunger assembly 204 is screwed onto housing 202 and plunger 214 is withdrawn outwards so that harpoon 216 clears opening 218 in housing 202. Then, penetrator cap 210 is removed from needle assembly 208, and shaft 220 is inserted into slot 222 in the housing (FIGS. 3 and 4). As shown in FIG. 5, opening 224 is sufficiently large for flange 226 to enter unobstructed.

Figure 8:
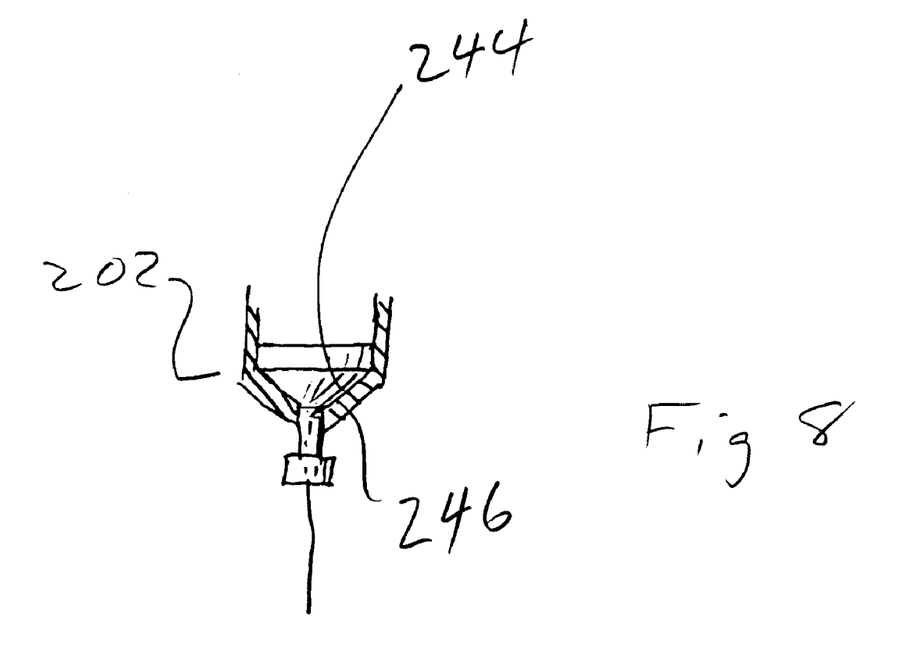
FIG. 8 is a elevation in section of the syringe body showing a needle assembly, not in section, fitted therein.

Next, medicine vial 230 is inserted into opening 218 and thumb ring 214 is pushed inwardly (FIG. 6), engaging harpoon 216 to piston 232 and driving the entire medicine vial 230 onto needle assembly 208. Rubber diaphragm 234 is penetrated by medicine penetrator 236, and vial end 238 is then pressed against flange 226, driving the needle assembly down behind fences 241 and 242 until, as shown in FIG. 8 in which the fences have been cut away, conical flange surface 244 mates to conical housing bottom 246 to seat the needle assembly firmly.

Figure 4A:
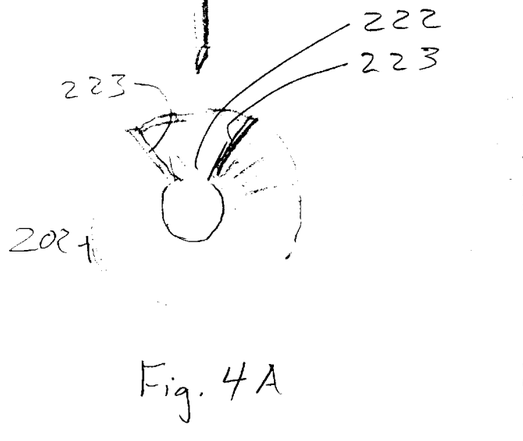
FIG. 4(a) is the bottom plan view of the syringe body.
Figure 4B:
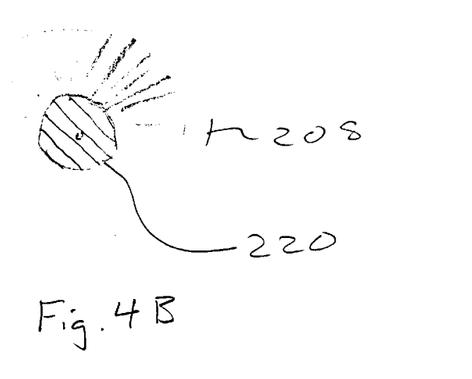
FIG. 4(b) is a bottom plan view of the needle assembly.

FIG. 4A shows a bottom plan view of housing 202. FIG. 4B is a bottom plan view of needle assembly 208 shown sectioned through the middle of shaft 220. Angled surfaces 223 (FIG. 4A) help guide shaft 220 (FIG. 4B) into slot 222 (FIG. 4A). FIG. 5 shows medicine vial 230 positioned above needle assembly 208 prior to driving of the plunger 214 against piston 232 and driving needle assembly 208 behind fences 241, 242 until conical flange surface 244 mates to the inner conical end 246 of housing 202, shown sectioned through its centerline in FIG. 8.

Figure 6:
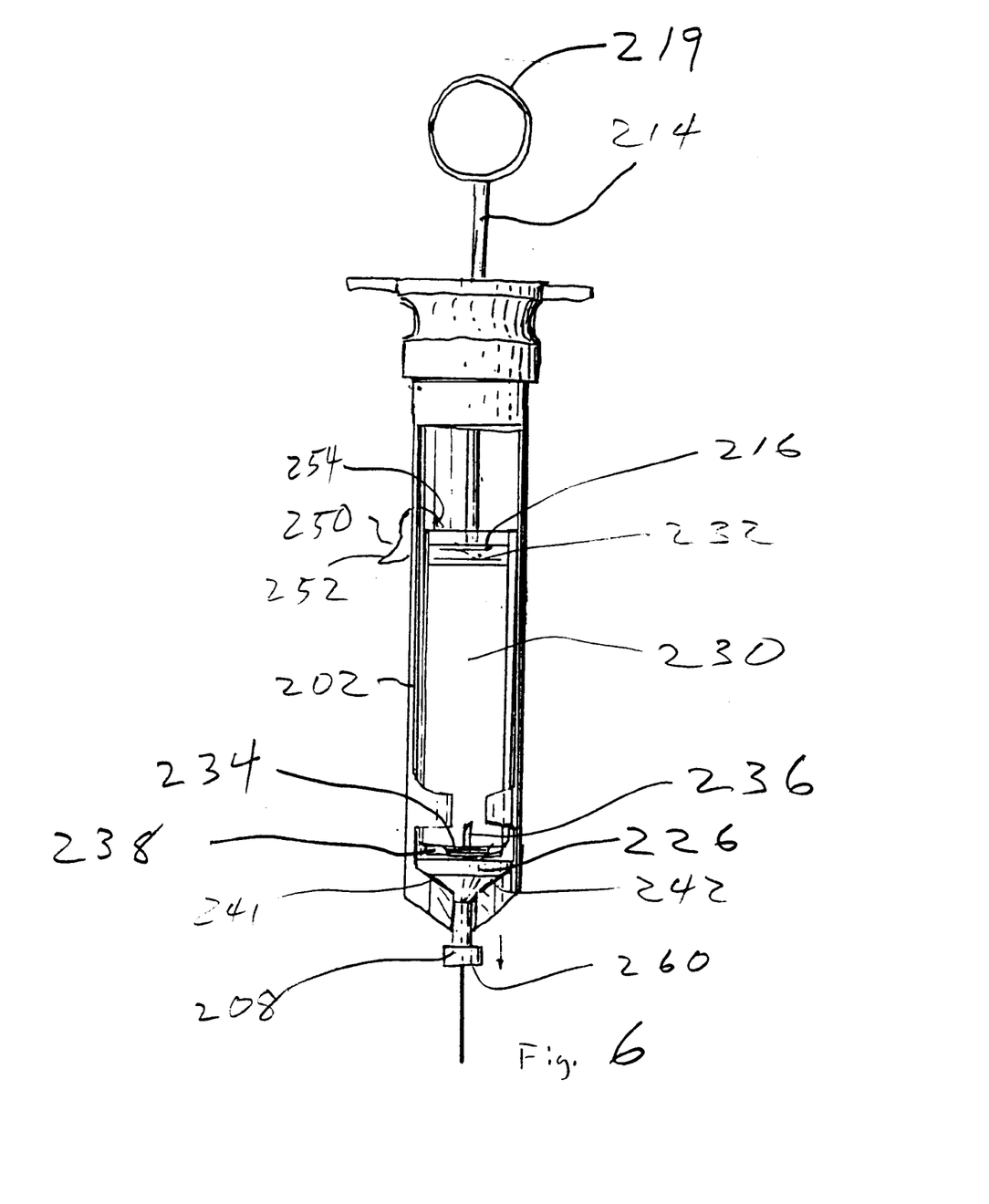
FIG. 6 is a similar elevation of the needle assembly being pressed down by the ampule into its working position.

As shown in FIG. 6, a latching mechanism such as 250, may be provided to lock medicine vial 230 in place, thereby holding the needle assembly 208 rigidly to housing 202. To remove the medicine vial, tab 252, on latch 250 may be pressed to disengage pawl 254 from the top of vial 230.

After plunger 214 is fully withdrawn, the harpoon can be disengaged from piston 232 and the medicine vial 230 can be pushed out of the syringe housing 202, and replaced with another vial for the same patient. Or, the entire housing 202 can then be autoclaved, after disposing of the needle assembly 208, which may be easily removed without vast pressure after the medicine vial 230 has been removed. To remove the needle assembly, push up on the lower flange 260 shown in FIG. 6 and then slide the assembly out of the slot. Medicine vials 230 may be changed with the same patient allowing continued use of the same needle assembly. After use, the vial 230 and needle assembly 208 are disposed of and the housing 202 and plunger assembly 204 are unscrewed and autoclaved.

Accordingly, while a few embodiments of the present invention have been shown and described, it is to be understood that many changes and modifications may be made thereunto without departing from the spirit and scope of the invention as defined in the appended claims.

Figure 9:
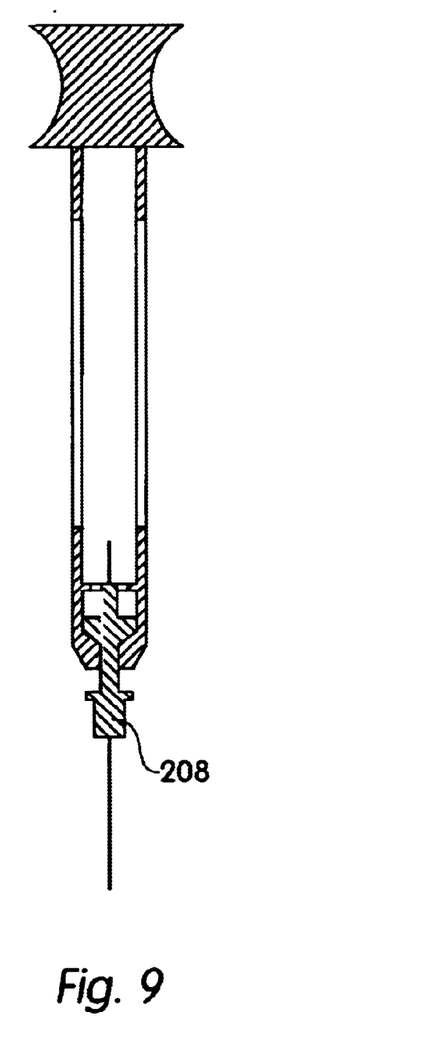
FIG. 9 is a similar view of the entire syringe as in FIG. 8, but entirely in section.
Figure 10:
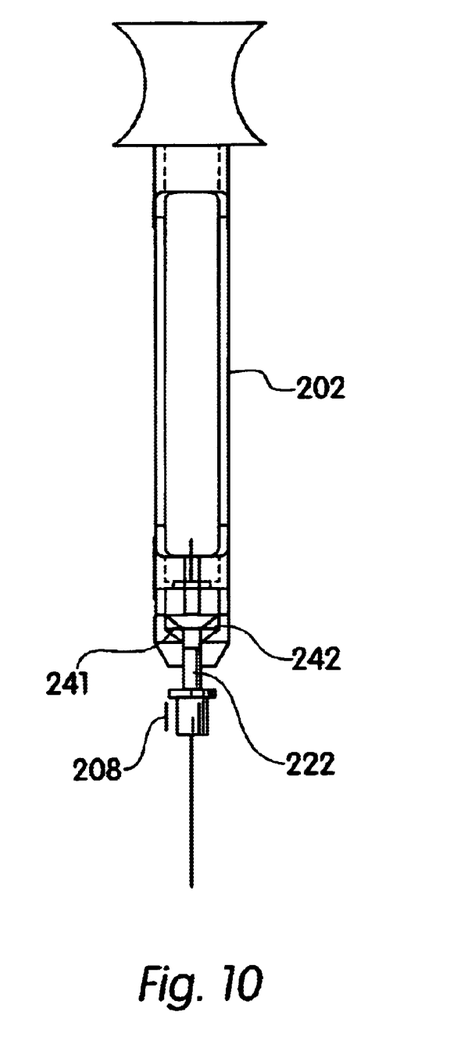
FIG. 10 is a similar view to FIG. 9, not in section.
Figure 11:
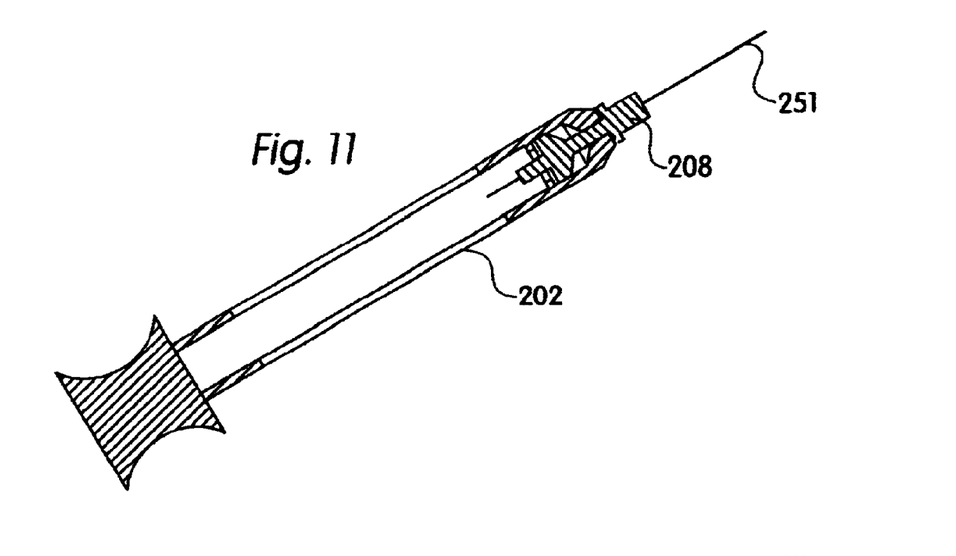
FIG. 11 is a similar view to FIG. 9, with the needle end displaced upwards.
Figure 12:
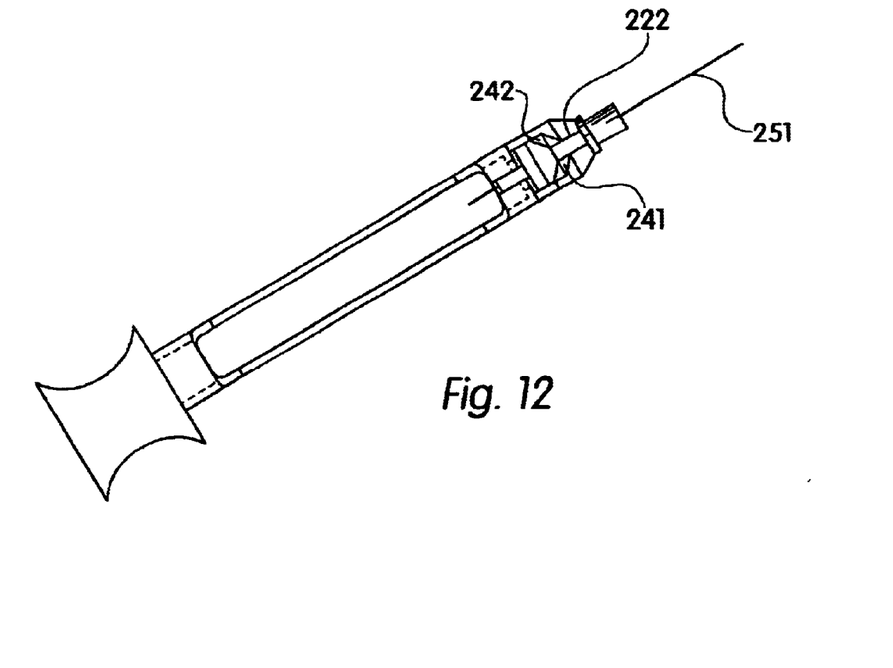
FIG. 12 is a similar view to FIG. 10, with the needle end displaced upwards.

In a configuration of needle assembly 208 shown in FIG. 8, FIGS. 9–10 show how, absent pressure from the vial 230, the needle assembly 208 is free to slide, as in FIGS. 11–12, plungerward of fences 241–242 when the housing 202 is tilted needle-up, about 30 degrees. When the housing 202 is then rotated about its needle axis 251 to orient slot 222 downward, the needle assembly 208 simply falls out, with no pressure except gravity. The dentist's hands need not touch the needle assembly 208.

What is claimed is:

1. A syringe, for injecting anesthetic contained in a medicine vial, said syringe including:
    a housing, said housing having a needle end and a plunger end, connected by a body;
    to which housing is attached a plunger assembly having a plunger at the plunger end;
    a vial slot in said housing, said slot cooperatively sized for receiving a medicine vial;
    a needle assembly slot, in the body, at the needle end, for receiving a needle assembly from a side of the body;
    a seat at said needle end for receiving and locating a corresponding seat portion of the needle assembly within the housing;
    whereby depressing the plunger housingward impales the vial onto a penetrator of the needle assembly, moves the needle assembly towards said seat, and seats the assembly firmly with said seat portion of the needle assembly against said seat.

2. A syringe according to claim 1 whereby removing the vial releases the needle assembly for removal.

3. The syringe according to claim 2 where removal is accomplished by:
    tilting the housing needle-up, toward the vertical, at least 30 degrees from the horizontal, until the needle assembly falls displacing the needle assembly seat away from the housing seat;
    then, rotating the needle assembly slot, about an axis formed by the needle, downward until the needle assembly falls out of the needle assembly slot.

4. A dental syringe system, for injecting anesthetic contained in a medicine vial, said syringe including:
    a housing, said housing having a needle end and a plunger end, connected by a body;
    to which housing is attached a plunger assembly having a plunger at the plunger end;
    a vial slot in said housing, said slot cooperatively sized for receiving a medicine vial;
    a needle assembly, said needle assembly having:
        a needle,
        a tapered needle seat,
        a penetrator opposite the needle,
        a penetrator cover,
        and a needle cover, joinable to the penetrator cover, to fully enclose and protect the needle assembly
    a needle assembly slot, in the body, at the needle end, for receiving a needle assembly from a side of the body;
    a seat at said needle end, cooperatively shaped for receiving and locating the tapered needle seat within the housing;
    whereby depressing the plunger housingward impales the vial onto a penetrator of the needle assembly, moves the needle assembly towards said seat, and seats the assembly firmly with said seat portion of the needle assembly against said seat.

5. The syringe according to claim 4 where removal is accomplished by:
    tilting the housing needle-up, toward the vertical, at least 30 degrees from the horizontal, until the needle assembly falls displacing the needle assembly seat away from the housing seat;
    then, rotating the needle assembly slot, about an axis formed by the needle, downward until the needle assembly falls out of the needle assembly slot.

6. A method of using a dental syringe comprising the following steps:
    Grasping a dental syringe for injecting anesthetic contained in a medicine vial, said syringe including a housing, said housing having a needle end and a plunger end, connected by a body; to which housing is attached a plunger assembly having a plunger at the plunger end; a vial slot in said housing, said slot cooperatively sized for receiving a medicine vial;
    withdrawing the plunger to a limit of travel,
    removing a penetrator cover from a needle assembly to uncover a needle assembly seat;
    sliding the needle assembly seat through a needle assembly slot in the housing; said needle assembly having clearance with an inside wall of the housing to provide a loose fit;
    seating the needle assembly seat against a housing seat whereby a cooperative taper on the needle assembly seat and on the housing seat locates the needle assembly firmly on the housing;
    inserting the medicine vial through a vial slot in the housing;
    depressing the plunger to impale the medicine vial on the penetrator, which seats the needle assembly seat even more firmly against the housing seat;

removing the needle cover;

injecting medicine from within the medicine vial into a patient;

withdrawing the needle from a patient; and sliding the medicine vial plungerward to remove the vial and to free the needle assembly together for disposal, due to its loose fit.

7. The syringe according to claim 6 where removal is accomplished by:

tilting the housing needle-up, toward the vertical, at least 30 degrees from the horizontal, until the needle assembly falls displacing the needle assembly seat away from the housing seat;

then, rotating the needle assembly slot, about an axis formed by the needle, downward until the needle assembly falls out of the needle assembly slot.

* * * * *